(12) United States Patent
Boudard et al.

(10) Patent No.: US 6,530,925 B2
(45) Date of Patent: Mar. 11, 2003

(54) EXTERNAL FIXATOR FOR IMMOBILIZING BONE FRAGMENTS, PARTICULARLY IN THE AREA OF THE WRIST

(75) Inventors: Frederic Boudard, La Garde (FR); Bertrand Fritsch, Toulon (FR); Christian Thomas, Toulon (FR); Elie Toledano, Toulon (FR); Christophe Lebrun, Tresserve (FR); Michel Berret, Toulon (FR); Jean-Jacques Martin, Bourg en Bresse (FR)

(73) Assignee: Fixano, Bourge en Bresse (FR)

( * ) Notice: Subject to any disclaimer, the term of this patent is extended or adjusted under 35 U.S.C. 154(b) by 0 days.

(21) Appl. No.: 09/835,486

(22) Filed: Apr. 17, 2001

(65) Prior Publication Data

US 2002/0004659 A1 Jan. 10, 2002

(30) Foreign Application Priority Data

Apr. 28, 2000 (FR) .............................. 00 05542

(51) Int. Cl.$^7$ .............................. A61B 17/64
(52) U.S. Cl. ........................................ 606/54
(58) Field of Search .............................. 606/54, 55, 57, 606/59

(56) References Cited

U.S. PATENT DOCUMENTS

| 4,135,505 A | | 1/1979 | Day |
| 4,554,915 A | * | 11/1985 | Brumfield |
| 4,628,919 A | * | 12/1986 | Clyburn |
| 5,403,313 A | | 4/1995 | Lin |
| 5,429,637 A | | 7/1995 | Hardy |
| 5,658,283 A | * | 8/1997 | Huebner ............ 606/57 |
| 5,662,649 A | * | 9/1997 | Huebner ............ 606/57 |
| 5,897,555 A | * | 4/1999 | Clyburn et al. ....... 606/54 |
| 5,941,877 A | | 8/1999 | Viegas et al. |
| 6,010,501 A | * | 1/2000 | Raskin et al. ........ 606/54 |
| 6,171,309 B1 | * | 1/2001 | Huebner ............ 606/57 |

FOREIGN PATENT DOCUMENTS

GB          2 077 847 A      12/1981

* cited by examiner

*Primary Examiner*—Ralph A. Lewis
(74) *Attorney, Agent, or Firm*—Oliff & Beridge, PLC

(57) ABSTRACT

This fixator (1) comprises a rigid bar (7), two pin-holder assemblies (8, 9) which can be moved relative to this bar (7), and means (13, 22) with which it is possible to immobilize each pin-holder assembly (8, 9) in a defined position relative to the bar (7).

According to the invention:

the bar (7) has a cylindrical main part (10) and a spherical part (11) at one end;

a first pin-holder assembly (8) comprises a one-piece body (12) with a bore passing through it to permit its engagement by sliding on the cylindrical part (10) of the bar (7); and the second pin-holder assembly (9) comprises a one-piece body (15) in which a recess (16) is formed, this recess (16) having a zone of partially spherical shape with a radius slightly greater than that of said spherical part (11), this zone being such that it can receive this spherical part (11) with pivoting, without lateral play, and with a possibility of articulation of said second pin-holder assembly (9).

9 Claims, 3 Drawing Sheets

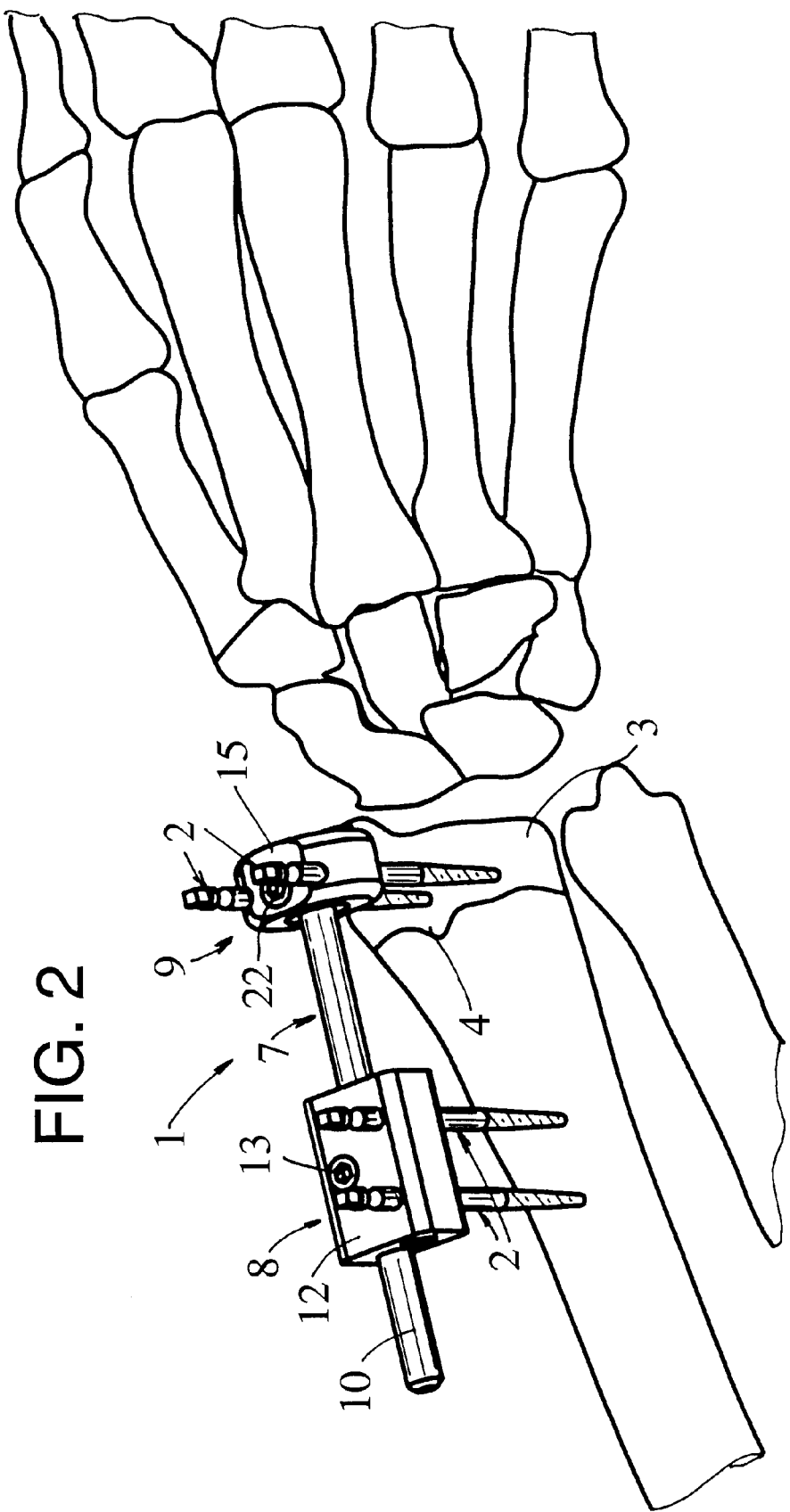

EXTERNAL FIXATOR FOR IMMOBILIZING BONE FRAGMENTS, PARTICULARLY IN THE AREA OF THE WRIST

BACKGROUND

1. Field of the Invention

The present invention relates to an external fixator for immobilizing bone parts, particularly in the area of the wrist.

2. Description of Related Art

A fixator exists with which it is possible to immobilize bone parts in the area of the wrist, comprising a bar and two pin-holder assemblies which can slide and pivot relative to this bar. To allow the pins to be oriented in all the desired directions depending on the immobilization to be performed, each pin-holder assembly is mounted on a slotted ring of spherical outer shape, engaged and able to slide on the bar, and comprises two jaws, one of which is intended to receive and clamp the pins, and the other of which is intended to surround and clamp this ring.

With the second jaw in the loosened state, the ring permits each pin-holder assembly to slide along the bar and allows this assembly to pivot about the ring in the three spatial planes. Tightening of this second jaw makes it possible, by clamping the ring on the bar, to immobilize each pin-holder assembly both in terms of sliding relative to the bar and in terms of pivoting relative to the ring.

This type of fixator is satisfactory in practice but has the disadvantage of having a relatively complex structure, which is not without impact on its production cost.

This fixator cannot therefore be provided to be discarded after a single use, which means that it has to be sterilized after each use. This sterilization involves dismantling and re-fitting the fixator, which are relatively awkward operations, and requires that the fixator be kept in a suitable sterile packaging between two uses.

SUMMARY OF THE INVENTION

The present invention aims to remedy these substantial disadvantages by making available a fixator whose structure is very simple and is inexpensive to manufacture, but which nonetheless has just as many possibilities of use, in particular as regards the possibilities of spatial orientation of the pins; this structure must in particular be such that the fixator can be provided to be discarded after a single use and can be supplied in a sterilized state ready for use.

The fixator concerned comprises, in a manner known per se, a rigid bar, two pin-holder assemblies which can be moved relative to this bar, and means with which it is possible to immobilize each pin-holder assembly in a defined position relative to the bar.

According to the invention:

- the bar has a cylindrical main part and a spherical part at one end;
- a first pin-holder assembly comprises a one-piece body with a bore passing through it to permit its engagement by sliding on the cylindrical part of the bar; and
- the second pin-holder assembly comprises a one-piece body in which a recess is formed, this recess having a zone of partially spherical shape with a radius slightly greater than that of said spherical part, this zone being such that it can receive this spherical part with pivoting, without lateral play, and with a possibility of articulation of said second pin-holder assembly.

This fixator therefore has a very simple structure and is particularly easy to manufacture. The resulting low cost allows this fixator to be used once and discarded and, consequently, makes it possible to eliminate all sterilization operations.

The first pin-holder assembly can slide and pivot relative to the bar and can therefore be placed in any required position relative to a long bone, in particular the humerus; the second pin-holder assembly is movable by pivoting relative to the bar in the three spatial planes, which permits any desired orientation of the pins, for insertion in the bone part concerned, in particular a fragment of the humerus or a metacarpal. The fixator according to the invention thus has very wideranging possibilities of movement of the pin-holder assemblies and of spatial orientation of the pins, so that its very simple structure, which is inexpensive to manufacture, does not in any way lessen its possibilities of use.

The pin-holder assemblies, by virtue of their one-piece structure, can be obtained by relatively simple cutting, drilling and tapping operations.

In addition, this fixator is quick and easy to dismantle and re-fit in a case where re-use is desired, involving sterilization.

The means by which it is possible to immobilize said first pin-holder assembly in a defined position relative to the bar preferably consist of a tapped hole formed substantially perpendicular to said bore and opening into the latter, and of a screw which can be received in this hole, this screw, when tightened, making it possible to clamp the bar in the bore.

The means by which it is possible to immobilize said second pin-holder assembly in a defined position relative to the bar can themselves consist, in an identical fashion, of a tapped hole formed substantially perpendicular to said recess and opening into the latter, and of a screw which can be received in this hole, this screw, when tightened, making it possible to clamp the spherical part of the bar in the recess.

In this case, the tapped hole opening into said recess is advantageously positioned relative to this recess in such a way that its axis is situated outside the center of said zone of partially spherical shape, toward the side of said body via which said spherical part is introduced into the recess.

The body of each pin-holder assembly preferably has at least one bore passing through it, to permit engagement of a pin, and at least one tapped hole substantially perpendicular to this bore and opening into the latter; each tapped hole receives a screw which, when tightened, makes it possible to clamp the pin in the corresponding bore in order to immobilize this pin in a defined position relative to said body.

The bar is advantageously made of a synthetic material molded to the desired shape.

This material is preferably a radiotransparent material, such as a composite material. This material is advantageously a resin reinforced with carbon fibers.

The pin-holder assemblies for their part can also be made of a synthetic material permitting sterilization by autoclave or gamma rays.

To ensure that it is clearly understood, the invention will again be described below with reference to the attached diagrammatic drawing which shows, by way of nonlimiting examples, two possible embodiments of the fixator concerned.

BRIEF DESCRIPTION OF THE DRAWINGS

FIG. 2 is a perspective view thereof, after it has been fitted on a fractured humerus;

DETAILED DESCRIPTION OF EXEMPLARY EMBODIMENTS

Figure 1:
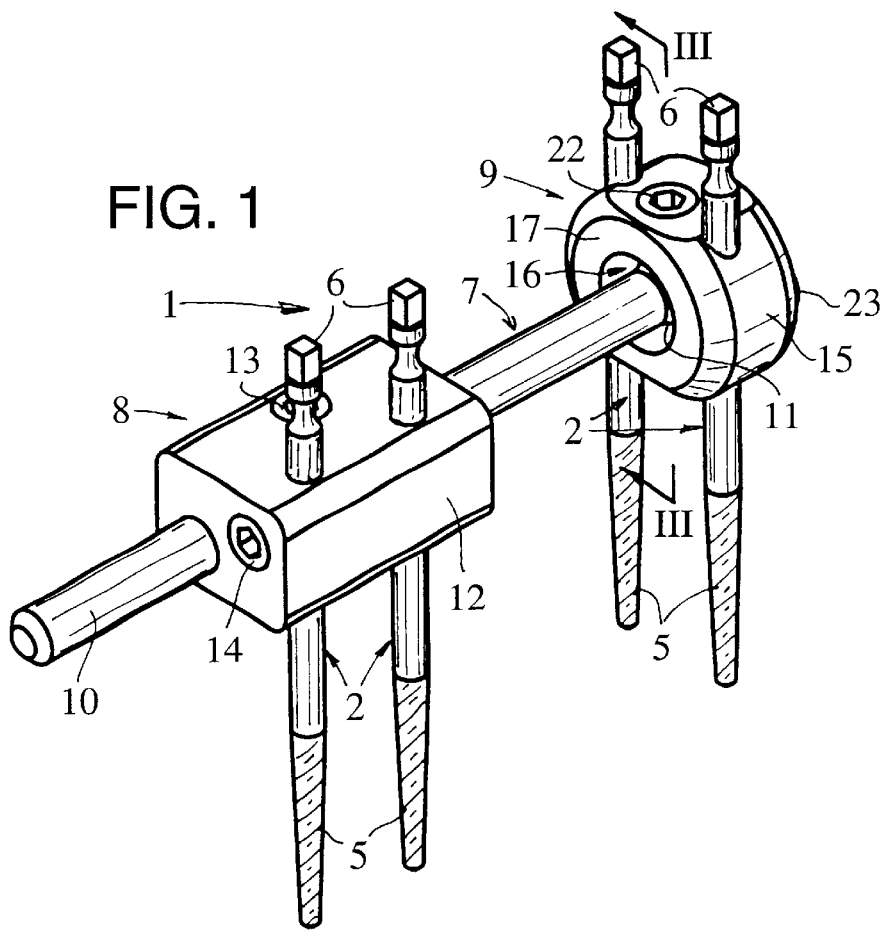
FIG. 1 is a perspective view thereof, according to a first embodiment.
Figure 3:
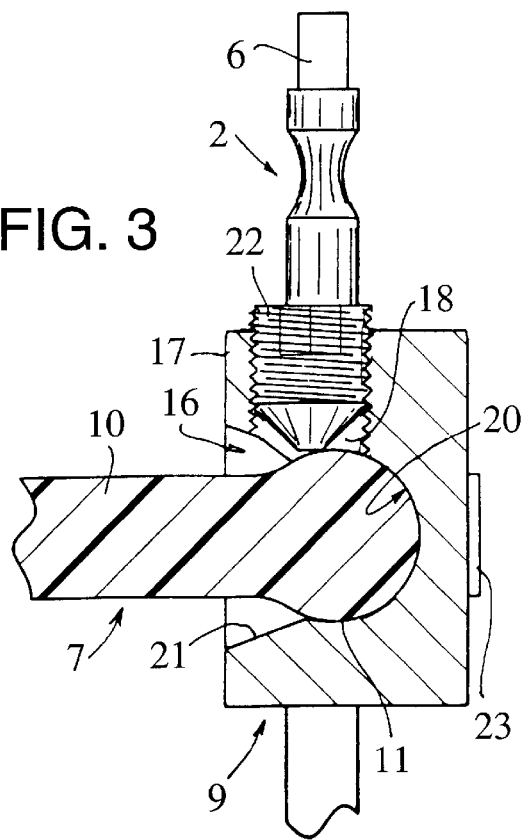
FIG. 3 is a view thereof on an enlarged scale, in cross section along the line III—III in FIG. 1.

FIGS. 1 to 3 represent an external fixator 1 with which it is possible to maintain two bone parts relative to one another by means of pins 2 inserted in these bone parts. In the example shown in FIG. 2, the fixator 1 is used to immobilize a humerus fragment 3 relative to the rest of the bone with a view to repairing the fracture 4.

The pins 2 are of conventional type. Each of them comprises a self-drilling part 5 permitting its insertion in the cortical substance of a bone, and a square head 6 allowing it to be maneuvered in rotation.

The fixator 1 comprises a rigid bar 7 and two pin-holder assemblies 8, 9.

The bar 7 is made of a resin reinforced with carbon fibers and is molded in such a way as to present a cylindrical main part 10 and a spherical part 11 at one end.

The assembly 8 comprises a one-piece body 12 made of synthetic or metal material.

This body 12 has a bore passing through it to permit its engagement by sliding on the part 10 and its pivoting about the latter, and a tapped hole formed perpendicular to this bore. This hole opens into the bore and receives a set screw 13 with a hexagonal cavity. This screw 13, when tightened, makes it possible to clamp the bar 7 in said bore in order to immobilize the body 12 in a defined position relative to this bar 7.

The body 12 additionally has two bores for sliding engagement of two pins 2, and two tapped holes, each of which is formed perpendicular to one of these bores. Each of these holes opens into the corresponding bore and receives a set screw 14 with a hexagonal cavity. These screws, when tightened, make it possible to clamp the pins 2 in said bores in order to immobilize these pins 2 in a defined position relative to the body 12.

The edges of the body 12 are rounded so as not to cause injury.

The assembly 9 also comprises a one-piece body 15 made of synthetic material or metal.

This body 15 has a general annular shape. It has a recess 16 which opens into one of its axial faces 17 and a tapped hole 18.

As is shown in FIG. 3, the recess 16 has a zone 20 of partially spherical shape with a radius slightly greater than that of said spherical part 11. This zone 20 has a shape such that it encloses more than half of the part 11 and is connected to the face 17 via a conical zone 21.

The hole 18 is formed radially relative to the recess 16 and opens into the latter. It is positioned in such a way that its axis is situated beyond the center of the zone 20, toward the zone 21.

This hole 18 and the recess 16 have respective dimensions which are such that the zone via which this hole 18 is connected to the recess 16 permits engagement of the part 11 in the recess 16 until this part 11 is received in the zone 20.

The aforementioned respective dimensions of the part 11 and of the zone 20 mean that this part 11 is received in the zone 20 without lateral play but with a possibility of articulation. The zone 21 forms a clearance which permits this articulation.

The hole 18 receives a set screw 22, with a hexagonal cavity, the radially internal end of this screw having a frustoconical shape. During tightening of this screw 22, this end will bear against the part 11 such that it is received in the zone 20 and makes it possible to clamp said part 11 in this zone 20 in order not only to immobilize the assembly 9 relative to this part 11 but also to ensure that the part 11 is retained in the recess 16.

The body 15 additionally has two bores for sliding engagement of two pins 2, and two tapped holes, each of which is formed perpendicular to one of these bores. Each of these holes opens into the corresponding bore and receives a set screw 23 with a hexagonal cavity. These screws 23, when tightened, make it possible to clamp the pins 2 in said bores in order to immobilize these pins 2 in a defined position relative to the body 15.

Figure 4:
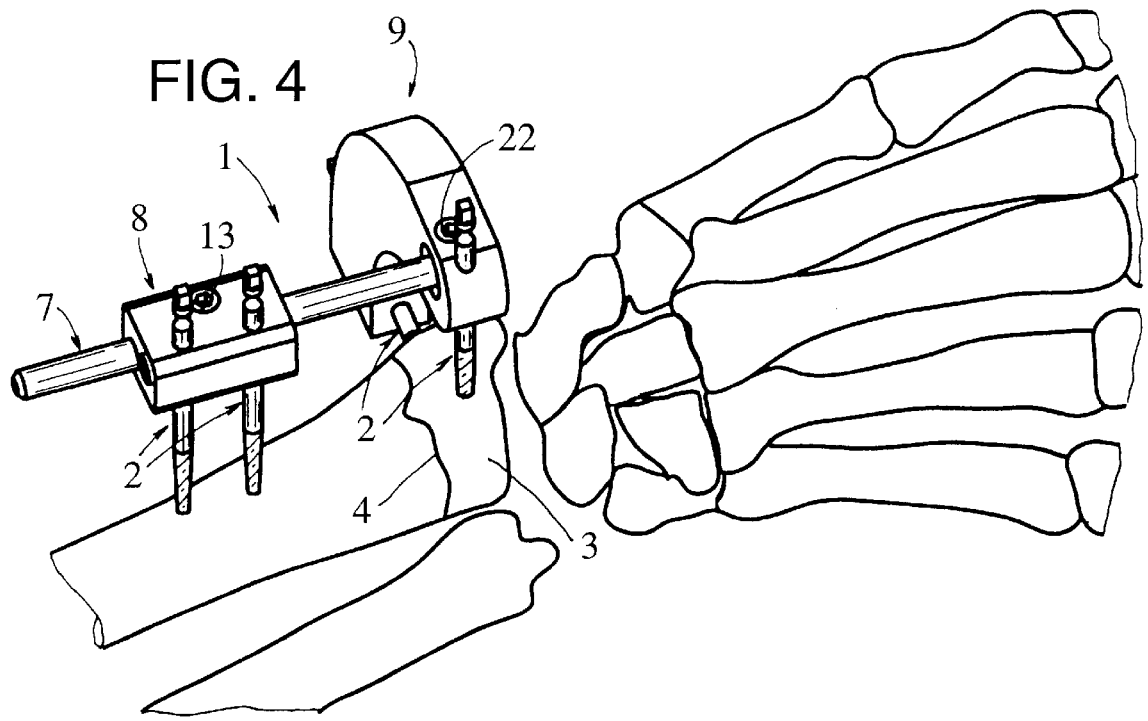
FIG. 4 is a perspective view thereof, according to a second embodiment, after it has been fitted on a fractured humerus.
Figure 5:
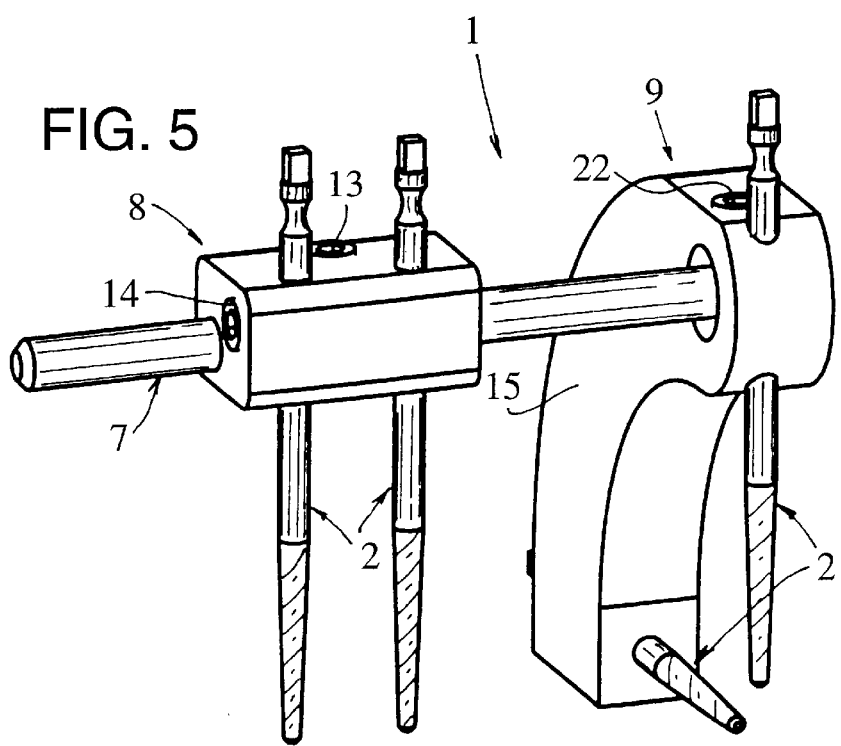
FIG. 5 is a perspective view thereof.

FIGS. 4 and 5 show a fixator 1 very similar to that which has just been described, and the elements or parts which are repeated here are designated by the same reference numbers as above.

In this case, the assembly 9 has a body 15 with a "crook" shape, and the bores receiving the pins 2 are formed at the ends of this "crook". These bores are thus perpendicular to one another, so that this assembly 9 permits positioning of perpendicular pins 2 if this proves necessary for the fixation which is to be performed.

It will be evident from the above that the invention makes available a fixator whose structure is very simple and inexpensive to manufacture, but nonetheless has just as many possibilities of use, particularly as regards the possibilities of spatial orientation of the pins 2. This structure in particular means that the fixator can be discarded after one use and can be supplied in a sterilized state, ready for use.

What is claimed is:

1. An external fixator for immobilizing bone parts comprising a longitudinally extending, two pin-holder assemblies which can be moved relative to this bar, and means for immobilizing each pin-holder assembly in a defined position relative to the bar; wherein:

the bar has a cylindrical main part and a spherical part at one end of the bar;

a first pin-holder assembly of the two pin-holder assemblies comprises a one-piece body with a bore passing through it to permit its engagement by sliding on the cylindrical part of the bar; and a second pin-holder assembly of the two pin-holder assemblies comprises a one-piece body in which a recess is formed, this recess having a zone of partially spherical shape with a radius slightly greater than that of said spherical part, this zone being such that it can receive this spherical part with pivoting, without lateral play, and with a possibility of articulation of said second pin-holder assembly, the one-piece body of the second pin-holder assembly being configured to receive at least one pin such that the at least one pin extends through the one-piece body at a same longitudinal position as the recess.

2. The fixator as claimed in claim 1, wherein the means for immobilizing said first pin-holder assembly in a defined position relative to the bar consist of a tapped hole formed substantially perpendicular to said bore and opening into the latter, and of a screw, which can be received in this hole, this screw, when tightened, making it possible to clamp the bar in the bore.

3. The fixator as claimed in claim 1, wherein the means for immobilizing said second pin-holder assembly in a defined position relative to the bar consist of a tapped hole formed substantially perpendicular to said recess and opening into the latter, and of a screw which can be received in this hole, this screw, when tightened, making it possible to clamp the spherical part of the bar in the recess.

4. The fixator as claimed in claim 3, wherein the tapped hole opening into said recess in such a way that its axis is situated outside the center of said zone of partially spherical shape, toward the side of said body via which said spherical part is introduced into the recess.

5. The fixator as claimed in claim 1, wherein the body of each pin-holder assembly has at least one bore passing through it, to permit engagement of a pin, and at least one tapped hole substantially perpendicular to this bore and opening into the latter; each tapped hole receives a screw which, when tightened, makes it possible to clamp the pin in the corresponding bore in order to immobilize this pin in a defined position relative to said body.

6. The fixator as claimed in claim 1, wherein the bar is made of a synthetic material molded to the desired shape.

7. The fixator as claimed in claim 6, wherein the bar is made of a radiotransparent material.

8. The fixator as claimed in claim 6, wherein the bar is made of a resin reinforced with carbon fibers.

9. The fixator as claimed in claim 1, wherein the pin-holder assemblies are made of a synthetic material permitting sterilization by autoclave or gamma rays.

* * * * *